US00PP28792P3

(12) United States Plant Patent
Gerdts et al.

(10) Patent No.: US PP28,792 P3
(45) Date of Patent: Dec. 26, 2017

(54) PEACH TREE NAMED 'BURPEACHTHIRTYNINE'

(50) Latin Name: *Prunus persica*
Varietal Denomination: Burpeachthirtynine

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 44 days.

(21) Appl. No.: 14/999,252

(22) Filed: Apr. 14, 2016

(65) Prior Publication Data
US 2017/0303453 P1 Oct. 19, 2017

(51) Int. Cl.
*A01H 5/08* (2006.01)

(52) U.S. Cl.
USPC ..... Plt./195

(58) Field of Classification Search
USPC ..... Plt./194, 195
See application file for complete search history.

*Primary Examiner* — Susan McCormick Ewoldt
(74) *Attorney, Agent, or Firm* — Randall Danskin P.S.

(57) ABSTRACT

A new and distinct variety of peach tree (*Prunus persica*), which is denominated varietally as 'Burpeachthirtynine', and which produces an attractively colored white fleshed, clingstone peach which is mature for harvesting and shipment approximately May 25 to June 5 under the ecological conditions prevailing in the San Joaquin Valley of central California.

1 Drawing Sheet

Latin name: *Prunus persica.*
Varietal Denomination: 'Burpeachthirtynine'.

BACKGROUND OF THE NEW VARIETY

The present variety of peach tree resulted from an ongoing program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled, and hybrid cross pollinations, each year, in order to produce seedling populations from which improved progenies are evaluated and selected.

The seedling, 'Burpeachthirtynine' was originated by us, and selected from a population of seedlings growing in our experimental orchards which are located near Fowler, Calif. The seedlings, grown on their own roots, were derived from planting seed derived from an unpatented peach tree which has been designated by us as 'D2.054', and which further produces yellow fruit. The pollen parent was a 'Galaxy' Peach Tree (USDA, unpatented). Fruit was collected from the female parents and seeds were later extracted. After a period of stratification, the seed was placed in our greenhouse, by population, and then field planted for tree establishment, and ultimately to exhibit fruit for evaluation. One seedling which produced yellow-fleshed fruit, which is the present variety, exhibited especially desirable characteristics, and was then designated as 'N52.122'. This seedling was marked for subsequent observation. After the 2007 fruiting season, the new variety of peach tree was selected for advanced evaluation, and repropagation. Generally speaking, and in comparison to the female parent, the current variety of peach tree produces fruit which has an earlier ripening date (approximately 1 week), and is saucer (donut) shaped. Still further the fruit is white-fleshed, and globose shaped. The aforementioned characteristics are different than the fruit produced by the female (unpatented) parent, 'D2.054'. Additionally the fruit produced by the new variety of peach tree is more rounded in shape, flavorful, and exhibits a more external reddish blush than the fruit produced by the 'Galaxy' peach tree, and which is the male parent.

ASEXUAL REPRODUCTION

Asexual reproduction of this new and distinct variety of peach tree was accomplished by bud grafting the new peach tree onto 'Nemaguard' Rootstock (un-patented). This was performed by us in our experimental orchard which is located near Fowler, Calif. Subsequent evaluations of these asexually reproduced plants have shown that those asexual reproductions run true to the original tree. All characteristics of the original tree, and its fruit, were established, and appear to be transmitted through these succeeding asexual propagations.

SUMMARY OF VARIETY

'Burpeachthirtynine' is a new and distinct variety of peach tree, which is considered of relatively large size, and which further has a vigorous growth characteristic. The new tree produces white-fleshed, low acid, saucer-shaped fruit which have a very good flavor, and eating qualities. This new peach tree has a medium chilling requirement of approximately 600 hours, and further produces relatively uniformly sized fruit throughout the tree's canopy. In addition to the foregoing, the fruit of the new peach tree also appears to have good handling and shipping qualities. The 'Burpeachthirtynine' peach tree additionally bears fruit which are typically ripe for commercial harvesting and shipment on approximately May 25 to June 2 under the ecological conditions prevailing in the San Joaquin Valley of central California. In relative comparison to the 'Galaxy' peach tree (U.S.D.A. unpatented), and which is the closest known variety, and the male parent, the new variety of peach tree bears fruit that ripens some 5-7, or more days, earlier. Further, the new variety does not exhibit 'stem pull', that is, fruit skin torn from the stem cavity upon picking. Moreover, the new variety exhibits a higher percentage of reddish blush on the skin of the fruit. In addition to the foregoing, the new variety of peach tree produces fruit that is considered a true clingstone. This is contrast to the fruit produced by the 'Galaxy' peach tree (unpatented).

BRIEF DESCRIPTION OF THE DRAWING

The accompanying drawing, which is provided, is a color photograph which depicts the fruit which is harvested from the new peach tree variety. The photograph depicts two whole mature fruit which are viewed from the apical and basal aspects. Additionally, one mature fruit is bisected in the sagittal or sutural plane, and displays the flesh color, and the exposed stone characteristics thereof. The external coloration of the fruit as shown in the photograph, is sufficiently matured for harvesting and shipment. The colors in this photograph are as nearly true as is reasonably possible in a color representation of this type. Due to chemical development, processing and printing, the leaves, and fruit depicted in these photographs may, or may not, be accurate when compared to the actual specimen. For this reason, future color references should be made to the color plates as provided in Royal Horticultural Society, Fourth Edition, 2004, and the general color descriptions as indicated, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will in the future display all the botanical, pomological or other characteristics as set forth, hereinafter. Therefore, this disclosure may not be relied upon to support any future legal claims including, but not limited to, a breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following was observed during the 7th fruiting season, and under the ecological conditions prevailing at the orchards of the assignee, and which are located near the town of Fowler, county of Fresno, state of California. All major color code designations are by reference to The R.H.S. Color Chart (Fourth Edition, 2001) provided by The Royal Horticultural Society of Great Britain. Common color names are also occasionally used.

Tree:

*Size*.—Generally considered medium-large, to large, in its growth pattern as compared to other common commercial peach cultivars ripening in the late season of maturity. The tree of the present variety was pruned to a height of approximately 270.0 cm. to about 310.0 cm. at commercial maturity.

*Width*.—Approximately 285.0 cm.

*Vigor*.—Considered vigorous. The present peach tree variety grew from about 180.0 cm. to about 200.0 cm. in height during the first growing season. The new variety was pruned to a height of approximately 170.0 cm. during the first dormant season, and primary scaffolds were then selected for the desired tree structure.

*Productivity*.—Productive. The fruit set varies from more than the desired crop load, to levels higher than desired amounts, when the new variety of peach tree is grown in a suitable horticultural zone, and under appropriate commercial nursery conditions. The fruit set is spaced, by thinning, so as to develop the remaining fruit into the desired market-sized fruit. The number of the fruit set varies with the prevailing climatic conditions, and the horticultural practices which are employed.

*Fruit bearing*.—Regular. The fruit set has been more than adequate during the previous years of observation, and thinning was necessary during the past 7 years on both the original seedling and on subsequent asexually reproduced trees.

*Tree form*.—Upright, and pruned into a vase shape.

*Density*.—Considered moderately dense. It has been discovered that pruning the branches from the center of the tree to obtain a resulting vase shape allows for enhanced air movement, and appropriate amounts of sunlight to improve fruit color, and the renewal of fruiting wood throughout the tree.

*Hardiness*.—The present peach tree was grown and evaluated in USDA Hardiness Zone 9. The calculated winter chilling requirements of the new tree is approximately 600 hours at a temperature at or below 7.0 degrees C. The present peach tree variety appears to be hardy under typical central San Joaquin Valley climatic conditions.

Trunk:

*Diameter*.—Approximately 18.5 cm in diameter when measured at a distance of approximately 15.24 cm. above the soil level. This measurement was taken at the end of the 7th growing season.

*Bark texture*.—Considered moderately rough, with folds of papery scarfskin being present. Since the bark development, and bark coloration change with advancing tree age this characteristic varies with the tree vigor, age and regional conditions where the tree is grown. Therefore, this tree characteristic is not a dependable descriptor of the new variety.

*Lenticels*.—Flat, oval lenticels are present on the trunk but are not abundant. The lenticels range in size from approximately 4.0 millimeters to about 6.0 mm. in width, and between about 2.0 and about 3.0 millimeters in height. The development and size of the trunk lenticels can be influenced, to some degree, by the ambient growing conditions. Consequently this is not, necessarily, a dependable and distinguishing characteristic of this peach tree variety. As trees of this new variety mature, lenticels are present, but they are generally covered by increasing layers of cork (mature bark), and therefore become less apparent.

*Lenticel color*.—Considered an orange-brown, (RHS Greyed-Orange Group N167 B).

*Bark coloration*.—Variable, but it is generally considered to be a grey-brown, (RHS Grey-Brown Group N200 B). This bark description was taken from trees in their seventh leaf which have ruptured the scarf skin, and which further, also, have developed bark furrowing which is much more typical of the bark of older trees.

Branches:

*Size*.—Considered medium large for the variety.

*Diameter*.—Average as compared to other peach tree varieties. The branches typically have a diameter of about 12.0 centimeters when measured during the 8th year after grafting.

*Surface texture*.—Average, and appearing furrowed on wood which is several years old.

*Crotch angles*.—Primary branches are considered variable, and are usually found growing at an angle of about 48 to about 57 degrees when measured from a horizontal plane. This characteristic can be influenced, to some degree, by tree vigor, rootstock and other horticultural conditions.

*Current season shoots*.—Surface texture — Substantially glabrous.

*Internode length*.—Approximately 2.6 cm.

*Color of mature branches*.—Approximately grey brown, (RHS Greyed-Brown Group 199 D).

*Current season's shoots*.—Color. — Medium green, (RHS Green Group 143 C). The color of new shoot tips is considered a bright and shiny green (RHS Yellow-Green Group 147 C). The vegetative shoot color can be significantly influenced by plant nutrition, irrigation practices, and the exposure of the tree to sunlight, and therefore should not be considered a consistent botanical characteristic of this new variety.

Leaves:

*Size*.—Considered medium-large for the species. Leaf measurements have been taken from vigorous, upright, current-season growth, at approximately mid-shoot. It should be understood that the leaf size is often influenced by prevailing growing conditions, quality of sunlight, and the location of the leaf within the tree canopy. For this reason, leaf sizes can vary, sometime significantly, based upon the ambient, and other horticultural factors listed, above, and therefore are not typically considered a dependable botanical descriptor.

*Leaf length*.—Approximately 163.0 to about 175.0 millimeters.

*Leaf width*.—Approximately 33.0 to about 37.0 millimeters.

*Leaf base*.—Shape. — The leaves generally exhibit equal marginal symmetry relative to the leaf longitudinal axis.

*Leaf form*.—Lanceolate.

*Leaf tip form*.—Acuminate.

*Leaf color*.—Upper Leaf Surface — A dark, yellow-green, (approximately RHS Green Group 139 B).

*Leaf texture*.—Glabrous.

*Leaf color*.—Lower Leaf Surface — A light to medium green, (approximately RHS Green Group 139 C).

*Leaf venation*.—Pinnately veined.

*Mid-vein*.—Color — Considered almost a light yellow, (approximately RHS Green-White Group 157 C) in the early, to mid-period of the growing season.

*Leaf margins*.—Gently undulating. Form. — Considered finely crenate. Uniformity. — Considered generally uniform.

*Leaf petioles*.—Form. — Considered canaliculated, and having a more pronounced trough when viewed from the dorsal aspect. The petiole margin is considered rounded when viewed from the ventral aspect. Size. — Considered medium-large for the species. Length — About 6.0 to about 9.0 mm. Diameter. — About 1.5 to about 2.0 mm. Color. — A light yellow-green, (approximately RHS Green Group 138 C).

*Leaf glands*.—Size. — Considered small for the species; approximately 1.5 mm. in length; and about 1.0 mm. in height. Number. — Generally one, and less commonly two glands appear per marginal side. Observations of more than two glands per marginal side are very uncommon. Type. — Glands located at the base of the leaf are predominantly reniform in shape. An additional one to two, and rarely more than two glands, which appear globose, and stalked in shape, are often present, and observed at the basal margin of the leaf petiole, as well. Color. — Considered a medium-dark brown, approximately (RHS Greyed-Green Group 196 C). Typically, the coloration of the glands darkens, and occasionally begins to desiccate during, and thereafter, the mid-late growing season.

*Leaf stipules*.—Size. — Medium for this variety. Number. — Typically 2 per leaf bud, and up to 6 per shoot tip are observed. Form. — Lanceolate, and having a serrated marginal edge. Color. — Green, (approximately RHS Green Group 143 C) when young, but graduating to a brown color, (approximately RHS Greyed-Orange Group 165 B) with advancing senescence. The leaf stipules are generally considered to be early deciduous.

Flower buds:

*Hardiness*.—No winter injury (bud death) has been noted during the last several years of observation in the central San Joaquin Valley. The new variety of peach tree has not been intentionally subjected to drought, cold or heat stress, and therefore this information is not available.

*Flower bud*.—Size — Variable, and dependent on the state of maturity. The flower buds as described were observed approximately 7 days prior to bloom.

*Flower bud*.—Length — Approximately 14.0 millimeters.

*Flower bud*.—Diameter — Approximately 11.0 millimeters.

*Flower bud surface texture*.—Pubescent.

*Flower bud orientation*.—Considered appressed, but appearing less so as the blossoms near opening.

*Bud scale color*.—Approximately RHS Greyed-Orange 175 C.

Flowers:

*Date of first bloom*.—Observed on Feb. 21, 2015.

*Blooming time*.—Considered average in relative comparison to other commercial peach cultivars grown in the central San Joaquin Valley. The date of full bloom was observed on Mar. 1, 2015. The date of full bloom varies slightly with the ambient climatic conditions, and prevailing horticultural practices that are employed.

*Duration of bloom*.—Approximately 9 or more days. This particular characteristic varies slightly with the prevailing climatic conditions.

*Flower class*.—Considered a perfect flower, complete and perigynous.

*Flower type*.—The variety is considered to have a showy type flower.

*Flower size*.—Considered medium-large for the species. The flower diameter, at full bloom, is approximately 44.0 to 48.0 millimeters.

*Bloom quantity*.—Considered abundant.

*Flower bud frequency*.—Generally two flower buds appear per node. On occasion one flower bud per node is observed.

*Petal size*.—Generally considered medium for the species. Petal Length. — Approximately 22.0 to 24.0 millimeters. Petal Width. — Approximately 19.0 to 22.0 millimeters.

*Petal form*.—Considered broadly ovate.

*Petal count*.—Nearly always 5.

*Petal texture*.—Glabrous.

*Petal color*.—Considered a light pink at the popcorn stage, (RHS Red-Purple Group 65 B), and darkening, with advanced senescence, and with the exposure to sunlight, to a medium-dark pink, (RHS Red-Purple 65 A).

*Fragrance*.—Slight.

*Petal claw*.—Form. — The claw is considered ovate, and is generally medium in size. Length. — Approximately 12.0-14.0 millimeters. Width. — Approximately 10.0 to 12.0 millimeters.

*Petal margins*.—Generally considered variable, from nearly smooth to slightly undulate.

*Petal apex*.—Considered entire. No apical trough has been observed in this variety.

*Flower pedicel*.—Length. — Considered medium for the species with an approximate length of about 2.5 to about 3.0 millimeters. Diameter. — Approximately 2.0 millimeters. Color. — A medium-brown, approximately (RHS Grey-Brown Group 199 A). Observation of this color depends upon the pedicel, and fruit maturity, and the timing of the observation. Surface Texture. — Glabrous.

*Floral nectaries*.—Color. — Considered a very pale green, (approximately RHS Yellow-Green Group 145 D).

*Calyx*.—Surface Texture. — Generally glabrous. Color. — A dull, brown-red, (approximately RHS Greyed-Red Group 178 B).

*Sepals*.—Surface Texture. — The surface has a short, fine pubescent texture. Numbers. — 5 sepals are typically observed. Size. — Average for the species. Sepal Length. — Approximately 9.0-11.0 millimeters. Sepal Width. — Approximately 6.0 to 8.0 millimeters. Sepal Shape. — Generally obovate. Sepal Margin. — Considered smooth and entire. Sepal Color. — A dull maroon, (approximately RHS Greyed-Red Group 178 A).

*Anthers*.—Generally. — Average in size. Color. — Orange when viewed dorsally, and prior to dehiscence, (approximately RHS Greyed-Orange Group 168 B).

*Pollen production*.—Pollen is abundant, and has a yellow color, (approximately RHS Yellow-Orange Group 21 D).

*Fertility*.—Self-fertile.

*Filaments*.—Size. — Approximately 13.0 to 15.0 millimeters in length. Color. — Considered white to a pinkish-white, (RHS Red Purple Group 65 D).

*Pistil*.—Number. — Usually one, and only rarely more than one is observed. Generally. — Large in size. Length. — Approximately 16.0 to about 18.0 millimeters in length, including the ovary. Color. — Considered a very pale green, (approximately RHS Yellow-Green Group 154 D). Surface Texture. — The variety has a long pubescent pistil.

Fruit:

*Maturity when described*.—Firm ripe condition (shipping ripe).

*Date of first picking*.—Approximately May 25 to Jun. 5, 2015.

*Date of last picking*.—Jun. 8, 2015. The date of harvest can vary with the prevailing climatic conditions, crop loads, and horticultural practices which are employed.

*Size*.—Generally — Considered moderately large, and very uniform.

*Average cheek diameter*.—Approximately 76.0 to about 82.0 millimeters.

*Average axial diameter*.—Approximately 75.5 to about 80.0 millimeters.

*Typical weight*.—Approximately 155.0 grams. This characteristic is quite dependent upon the prevailing horticultural practices, fruit maturity, and ambient growing conditions. Therefore this characteristic is not particularly distinctive of the new variety.

*Fruit form*.—Generally — Considered saucer-shaped. The fruit is otherwise generally uniform in symmetry.

*Fruit suture*.—No stitching appears to exist along the suture line.

*Suture*.—Color — Generally, the fruit appears blushed to the same degree as the skin, (approximately RHS Greyed-Purple Group 185 A).

*Ventral surface*.—Form — Considered even, and uniform in appearance, when it is viewed from the lateral, sutural plane.

*Apex*.—Shape — Generally retuse.

*Base*.—Shape — Generally smooth.

*Stem cavity*.—Generally — The stem cavity extends in a rounded, circular form which is considered uniform. The stem cavity slightly extends toward the suture. The average depth of the stem cavity is about 7.0-9.0 mm. The average width of the stem cavity is about 25.0 mm. The average length of the stem cavity, when measured in the suture plane is about 39.0 mm.

*Fruit skin*.—Thickness. — Considered medium in thickness, and tenacious to the flesh. Surface Texture. — Short, fine and pubescent. The pubescence is moderately abundant. Taste. — Non-astringent. Tendency to crack. — Not observed in the previous years of observation and evaluation.

*Fruit skin color*.—Blush Color. — Generally speaking, a dull red blush exists on the skin of the fruit (approximately RHS Greyed-Purple Group 185 A), and is more typically present on the portions of the fruit facing the sunlight. The blush of the fruit typically covers approximately 85%-95% of the fruit skin surface. The percentage of the blush on the fruit skin surface can vary, and is generally dependent upon the fruit's exposure to direct sunlight; specific fruit maturity; and also the prevailing ecological and horticultural conditions under which the fruit was grown.

*Ground color*.—A medium-light yellow, (approximately RHS. Yellow-Green Group 145 D).

*Fruit stem*.—Size. — Moderately long in length, approximately 6.0 to about 9.0 millimeters. Diameter. — Approximately 2.5 to about 3.5 millimeters. Color. — Pale yellow-green, (approximately RHS Yellow-Green Group N144 D).

*Fruit flesh*.—Ripening. — Considered even. Texture. — Firm, crunchy, juicy and dense. Considered firm yet non-melting. Fibers. — Present, but not prominent. Aroma. — Slight. Eating Quality. — Considered very good. Flavor. — Considered balanced. Juice Production. — Moderate to abundant. Brix. — About 12.0 to 16.0 degrees. This characteristic varies slightly with the number of fruit per tree; the maturity of fruit when harvested; the prevailing cultural practices; and the ambient climatic conditions. Acidity. — Considered average. Approximately 0.25 titratable acidity is detected. Acid levels assayed from the fruit flesh can vary depending upon the fruit maturity, sunlight exposure, amber climatic conditions and other regional or horticultural influences. Typically titratable acidity will decrease after harvest, packing, shipment and the time to consumption. Flesh Color. — It is considered white, (approximately RHS White Group 155 A), and does not typically exhibit any pigmentation of red radiating from the stone.

Stone:

*Type*.—Considered a clingstone trust.

*Size*.—It is generally considered to be medium for the saucer phenotype of the species. The stone size varies, significantly, depending upon the tree vigor, the crop load, and the prevailing growing and horticultural conditions under which the tree was grown.

*Length*.—Average, about 11.0 to about 13.0 millimeters.

*Width*.—Average, about 23.0 to about 26.0 millimeters.

*Diameter*.—Average, about 23.0 to about 26.0 millimeters.

*Form*.—Roughly oblate.

*Stone base*.—Shape — The stone is considered shortly attenuate.

*Apex*.—Shape — The stone exhibits a refuse apex.

*Stone surface*.—Surface Texture — Generally considered irregularly furrowed toward the apex. Further, more pitting is observed in the mid-portion of the stone (laterally). Ridges. — Ridging is present but is not considered prominent, and is usually oriented parallel, and laterally relative to the ventral and dorsal margins. Ventral Edge. — The ventral edge is generally considered troughed with several substantial grooves that converge apically. Dorsal Edge. — Shape — Generally considered even. The folds of the surface ridges appearing on the external margins often end gently along the suture.

*Stone color*.—The color of a mature, dry stone is generally considered a dull brown, approximately (RHS Greyed-Orange Group 164 C).

*Tendency to split*.—Splitting has rarely been noted.

*Kernel*.—Length. — Approximately 8.0-10.0 millimeters. Width. — Approximately 12.0-15.0 millimeters. Thickness. — 5.0-6.0 millimeters. Size. — The kernel is considered medium in size. Form. — Considered generally oblate. It should be noted that the kernels from the vertically compressed stone cavity of a saucer-shaped species are most generally deformed. The kernels, therefore, are limited in the vertical space in which to develop seed length as compared to globose shaped fruit. The kernels, therefore, are very often shriveled, misshapen and generally non-viable in germination by employing conventional methods. Pellicle. — Slightly pubescent. Color. — A dark tan (RHS Greyed-Orange Group 165 B).

*Use*.—The present new variety of peach tree which is named 'Burpeachthirtynine' is considered to be a peach tree of the early, midseason of maturity, and which further produces fruit which are considered to be firm, attractively colored, and which are further useful for both local and long distance shipping.

*Keeping quality*.—Appears excellent. The fruit of the present variety of peach tree has stored well for periods of up to 35 days after harvest at 1.0 degree Celsius with no damage noted.

*Shipping quality*.—Good. The fruit of the new peach tree variety showed minimal bruising of the flesh or skin damage after being subjected to normal harvesting and packing procedures,

*Resistance to insects and disease*.—No particular susceptibilities were noted. The present variety has not been intentionally tested to expose or detect any susceptibilities or resistances to any known plant, fruit diseases, insect, frost, winter injury or other environmental factors. Although the new variety of peach tree possesses the described characteristics when grown under the ecological conditions prevailing near Fowler, Calif., in the Central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by plant Letters Patent is:

1. A new distinct variety of peach tree, substantially as illustrated and described, and which is characterized principally as to novelty by producing an attractively colored, saucer-shaped, white fleshed, clingstone peach which is mature for harvesting and shipment approximately May 25 to June 5 under the ecological conditions prevailing in the San Joaquin Valley of central California.

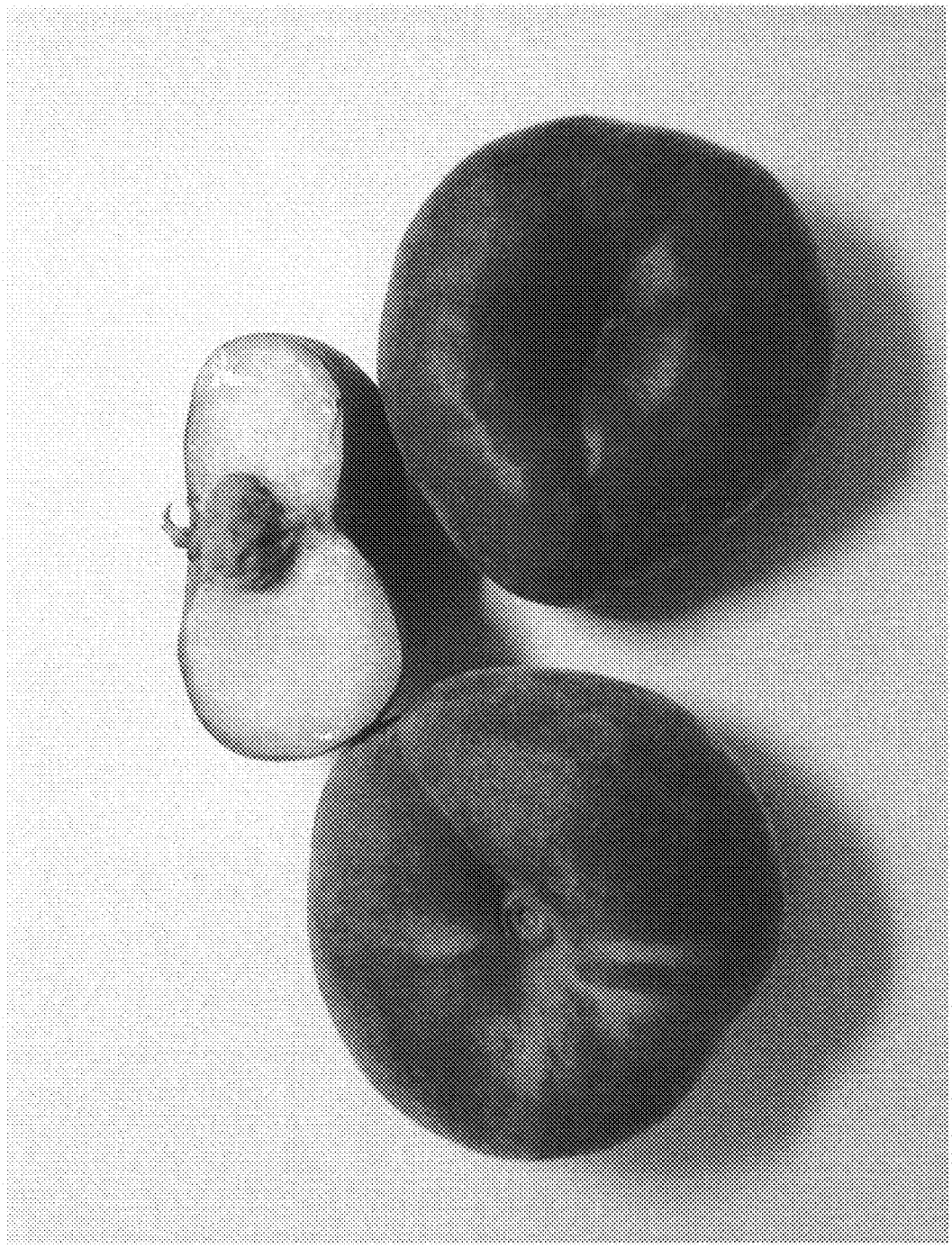

* * * * *